United States Patent [19]
Douglas et al.

[11] Patent Number: 5,426,230
[45] Date of Patent: Jun. 20, 1995

[54] PROCESS FOR THE PREPARATION OF 4-CHLORO-2-CYCLOPROPYLCARBONYLANILINE

[75] Inventors: Alan Douglas, Monmouth Junction; Ioannis Houpis, Plainfield; Audrey Molina, Elizabeth; Ralph P. Volante, Cranbury; Nobuyoshi Yasuda, Mountainside, all of N.J.

[73] Assignee: Merck & Co., Inc., Rahway, N.J.

[21] Appl. No.: 258,356

[22] Filed: Jun. 10, 1994

Related U.S. Application Data

[63] Continuation of Ser. No. 113,159, Aug. 27, 1993, abandoned.

[51] Int. Cl.⁶ ............................................. C07C 209/68
[52] U.S. Cl. .................................................. 564/442
[58] Field of Search ......................................... 564/442

[56] References Cited

FOREIGN PATENT DOCUMENTS 1545341 5/1979 United Kingdom .
WO93/04047 3/1993 WIPO .

OTHER PUBLICATIONS

March, Advanced Organic Chemistry, Fourth Edition (1992) p. 552.
Adachi, M. et al., ". . . Aminohaloborane in Organic Synthesis . . . " Chem. Pharm. Bull. Bol. 33, pp. 1826–1835 (1985).
Sugasawa, T. et al., ". . . Aminohaloborane in Organic Synthesis . . . " J. Am. Chem. Soc. 100, 4842 (1978).
Sugasawa, T. et al. ". . . Aminohaloborane in Organic Synthesis . . . " J. Org. Chem., vol. 44, No. 4., 578 (1979).
Harada, T. et al. ". . . The Catalytic Friedel-Crafts Acylation . . . " Synthesis, pp. 1216–1220 (Sep. 1991).
Mukaiyama, T. et al. ". . . The Catalytic Friedel-Crafts Acylatin Reaction . . . " Chemistry Letters, pp. 1059–1062, 1991.

Primary Examiner—Richard L. Raymond
Attorney, Agent, or Firm—Roy D. Meredith; Jack L. Tribble

[57] ABSTRACT

4-Chloro-2-cyclopropylcarbonylaniline is prepared by condensation of 4-chloroaniline with 4-chlorobutyronitrile to form a 2-(4-chlorobutyryl)-4-chloroaniline, followed by ring closure of the 4-chlorobutyryl group to a cyclopropylcarbonyl moiety.

5 Claims, No Drawings

PROCESS FOR THE PREPARATION OF 4-CHLORO-2-CYCLOPROPYLCARBONYLANILINE

This is a continuation of application Ser. No. 08/113,159 filed on Aug 27, 1993, now abandoned.

BACKGROUND OF THE INVENTION

This invention is related to Merck case 18727IA, U.S. Ser. No. 07/991,164, filed Dec. 16, 1992, now abandoned, U.S. Ser. No. 08/148,476; and U.S. Ser. No. 08/294,771.

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is reverse transcription of the RNA genome by a virally encoded reverse transcriptase to generate DNA copies of HIV sequences, a required step in viral replication. It is known that some compounds are reverse transcriptase inhibitors and are effective agents in the treatment of AIDS and similar diseases, e.g., azidothymidine or AZT.

This invention relates to an improved process for synthesizing the AIDS antiviral L-738,372, which is a chiral compound of the structure

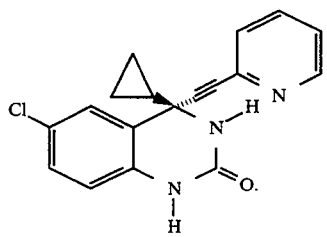

The substituted quinazoline L-738,372 is an exceptionally potent inhibitor of HIV reverse transcriptase. This activity of the compound makes it useful in the treatment or prevention of AIDS.

The present invention describes an improved synthesis of an intermediate for this compound. A prior method employs a Grignard reagent, which is unsuitable for commercial scale-up. The improved process of the present invention gives higher yields, and is an entirely different approach. In this invention there is a condensation of para-chloroaniline with cyanocyclopropane to give the desired intermediate 4-chloro-2-cyclopropylcarbonylaniline. Alternatively, but less preferably, para-chloroaniline is condensed with chlorobutyronitrile, followed by a second step of ring closure to form 4-chloro-2-cyclopropylcarbonylaniline.

SUMMARY OF THE INVENTION

This invention is concerned with an improved process for introducing the acyl function to the ortho-position of the aromatic amine in preparation of this cyclopropylcarbonylaniline intermediate. The improved process proceeds in higher yield without the use of a Grignard reagent which is incompatible with large scale industrial production. The improved process involves, instead, a condensation of para-chloroaniline with cyanocyclopropane to give the desired cyclopropylcarbonyl compound directly. Alteratively, in a two step sequence, para-chloroaniline is condensed with chlorobutyronitrile, then there is ring closure of the 4-chlorobutyryl group to form the desired cyclopropylcarbonyl compound.

DETAILED DESCRIPTION OF THE INVENTION

The novel process of this invention is illustrated by the reactions of the following scheme:

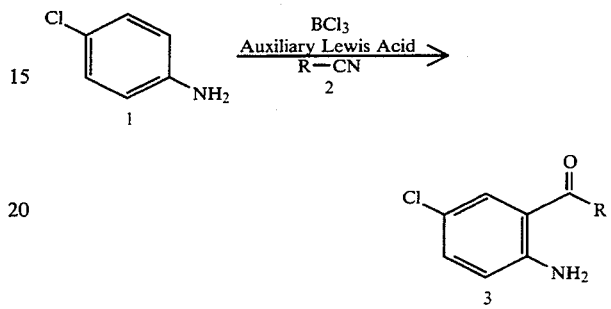

wherein R is

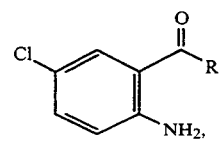

or -(CH$_2$)$_3$Cl

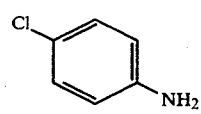

wherein R is

or (CH$_2$)$_3$Cl;

which comprises treating a mixture of boron trichloride and a compound of structural formula 1

in an organic solvent with a compound of formula RCN (2) and an auxiliary Lewis acid selected from aluminum trichloride, indium trichloride, ferric chloride and gallium trichloride at 15°–35° C., followed by heating at about 100°–130° C. for about 3–6 hours, to produce a compound of structural formula:

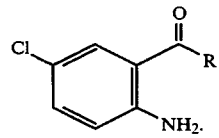

In one embodiment of this process, the 4-chloroaniline in an organic solvent such as methylene chloride, chlorobenzene, xylene, toluene or tetra-chloroethane is added slowly to a solution of boron trichloride in a similar organic solvent at about −10° C. to about 10° C. After warming to about 15 to 35° C., 4-chlorobutyronitrile is added. An auxiliary Lewis acid such as aluminum trichloride, indium trichloride, ferric chloride or gallium trichloride is then added with stirring and stirring is continued with heating for about 3–6 hours at 100 to 130° C. Stirring for about 4 hours at about 100° C. is preferred.

The intermediate, formed in this process after the addition of the auxiliary Lewis acid, is a compound of the structure

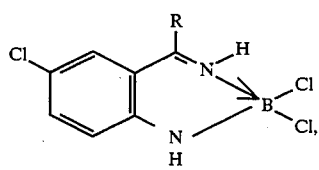

based on NMR studies.

In another embodiment of this process, the use of AlCl3 provides ketone 3 in yields of about 45%. On the other hand, using GaCl3 under similar conditions increases the yields of 3 to about 75%. Also, use of 2 moles (instead of 1.5 moles) of 4-chloroaniline per mole of nitrile further increases the yield to about 88–93%.

In another embodiment of this process, 4-chloroaniline in an organic solvent is added slowly to a solution of boron trichloride in an organic solvent at between about −20° C. and about 15° C. After warming to between about 15° C. and about 35° C., 4-chlorobutyronitrile (about 0.5 equivalent/equivalent 4-chloroaniline) is added. An auxiliary Lewis acid (about 0.55–0.6 equivalents) is then added with stirring and the stirring is continued at about 80°–140° C. for about 1 to 24 hours, preferably 3 to 6 hours. The organic solvents for this process include halogenated hydrocarbons, such as methylene chloride, 1,1,2,2-tetrachloroethane, 1,2-dichloroethane, or benzene derivatives, such as toluene, xylene, chlorobenzene, or mixture of these solvents. Other solvents may be suitable. The preferred solvent is toluene. The auxiliary Lewis acid is selected from aluminum trichloride, indium trichloride, ferric chloride, gallium trichloride, aluminum tribromide, gallium tribromide, ferric bromide, or indium tribromide. The preferred auxiliary Lewis acid is gallium trichloride.

The most preferred process is for the preparation of a compound of the structural formula:

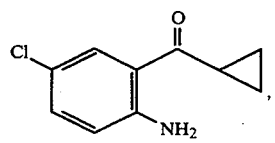

which comprises the steps of (a) mixing one equivalent of 4-chloroaniline in toluene with about one equivalent of BCl3 at a temperature range of about −10° to about 10° C., to give a mixture;

(b) warming the mixture to between about 15° and about 35° C.;

(c) adding thereto about 0.5 equivalents of 4-chlorobutyronitrile;

(d) adding about 0.55 equivalents of GaCl3;

(e) stirring for about 4 hours at about 100° C., to give compound 4.

In the process wherein R is −(CH2)3Cl, the next step to prepare the cyclopropylcarbonyl compound 4 comprises treating the purified or crude product 3 in an organic solvent such as THF, DMF or ether with potassium t-butoxide or other alkoxide salts at about room temperature (15°–30° C.). After completion of the reaction (about 30 minutes), it is quenched by the addition of water.

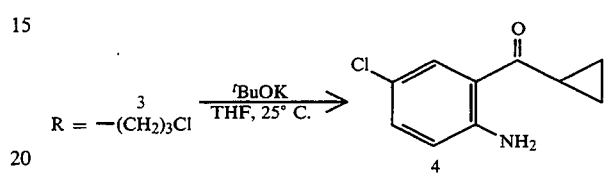

The intermediate 4 is useful in the synthesis of the reverse transcriptase inhibitor in accordance with the following reaction scheme, the steps of which are described in detail below.

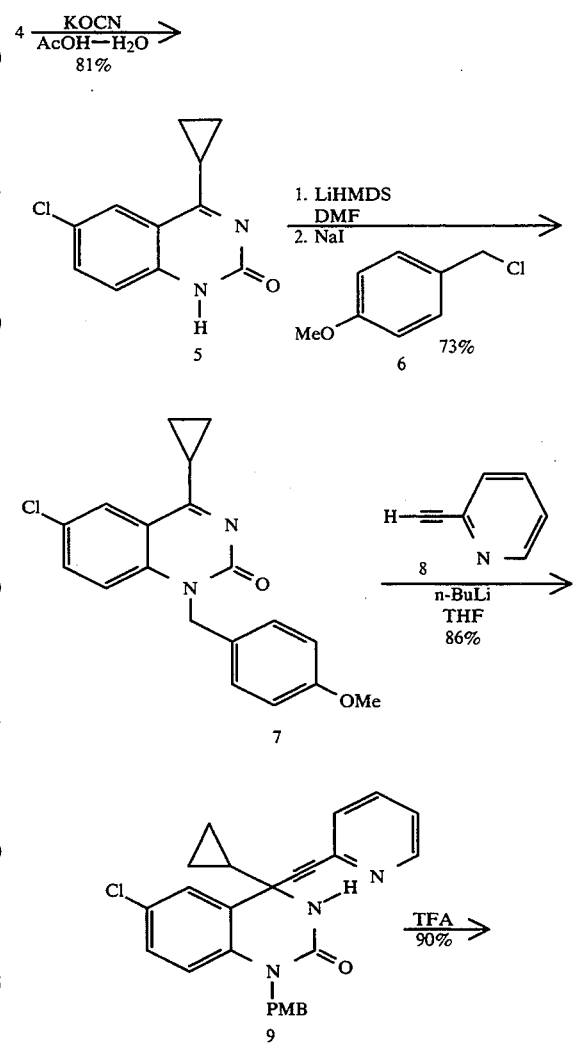

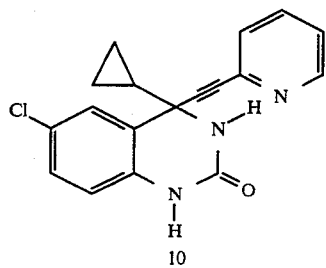

10

As mentioned previously, the ultimate product from the novel process of this invention is useful in the inhibition of HIV reverse transcriptase, the prevention or treatment of infection by human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by e.g., blood transfusion, exchange of body fluids through bites, accidental needle stick, or exposure to patient blood during surgery.

The particular advantage of the compound of this invention is its potent inhibition of HIV reverse transcriptase rendered resistant to other antivirals, such as 3-([[(4,7-dichloro- 1,3-benzoxazol-2-yl)methyl]-amino)-5-ethyl-6-methyl -pyridin-2(1H)-one; or 3-[2-1,3-benzoxazol-2yl)ethyl]-5-ethyl-6-methyl-pyridin-2(1H)-one; or AZT.

The ultimate product from the novel process of the present invention is also useful in determining the binding site of other antivirals to HIV reverse transcriptase, e.g., by competitive inhibition. Thus, the ultimate product of the process of this invention is a commercial product to be sold for these purposes.

For the purpose of treating AIDS or ARC, compound 10 may be administered orally, parenterally (including subcutaneous injections, intravenous, intramuscular, intrastemal injection or infusion techniques), by inhalation spray, or rectally, in dosage unit formulations containing conventional non-toxic pharmaceutically acceptable carders, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically effective amount of compound 10.

Compound 10 can be administered orally to humans in a dosage range of 0.1 to 100 mg/kg body weight in divided doses. One preferred dosage range is 0.1 to 10 mg/kg body weight orally in divided doses. Another preferred dosage range is 0.1 to 20 mg/kg body weight orally in divided doses. It will be understood, however, that the specific dose level and frequency of dosage for any particular patient may be varied and will depend upon a variety of factors including the age, body weight, general health, sex, diet, mode and time of administration, rate of excretion, drug combination, the severity of the particular condition, and the host undergoing therapy.

The present invention is also directed to combinations of compound 10 with one or more agents useful in the treatment of AIDS. For example, compound 10 may be effectively administered, whether at periods of pre-exposure and/or post-exposure, in combination with effective amounts of the AIDS antivirals, immunomodulators, antiinfectives, or vaccines.

EXAMPLE

Preparation of ketone 3 with Lewis acid AlCl3

To a 3-neck, round bottom flask equipped with an overhead stirrer, BCl3, (1M solution in CH2Cl2, 460 ml, 0.46 mol) was added, under N2, via addition funnel. After addition, the funnel was removed, under N2 purge, and replaced with a distillation condenser and trap for removal of methylene chloride. The apparatus was vented through an aqueous NaOH scrubber.

In a separate flask, chlorobenzene (260 ml) was added to 4-chloroaniline, 1, (80.0 g, 0.63 mol). Heating was needed in order to dissolve the aniline completely.

The 4-chloroaniline solution was cannulated into the BCl3 solution slowly at 0° C. The solution became a thick slurry which was warmed to RT followed by addition of neat 4-chlorobutyronitrile, 2, (37.4 ml, 0.42 mol) with no effect on temperature. Immediately after, solid AlCl3, under N2, was added at which time an exotherm of approximately 10° C. was observed and the slurry became homogenous. The reaction mixture was then heated at 100° C. and the methylene chloride was distilled. When the distillation was completed, the reaction mixture was heated at reflux (130° C.) for approximately 4 hours, and aged overnight at RT.

The reaction mixture was quenched with equal parts of THF and 1N HCl (300–500 ml) at ca. 25° C. (A cooling bath was used to control the resulting exotherm). A thick slurry formed during the quench which was dissolved by heating to about 60° C. The solution was allowed to cool to RT and was stirred for approximately 1 hour. It was then extracted with methylene chloride (ca 500 mL). The organic layer was washed with 1N HCl, dried over MgSO4, filtered and concentrated in vacuo. A $^1$H NMR of the crude concentrate showed the desired product, 3, (45% yield) and a trace of 4-chlorobutyronitrile. The crude product was used as such in the following reaction.

Alternate Preparation of Ketone 3 with Lewis acid GaCl3

To a dry 50 L three neck round bottom flask, equipped with a 10 L dropping funnel, an overhead stirrer, a thermocouple probe, a reflux condenser, a bubbler, a nitrogen inlet and a scrubber, was charged 10.6 L of dry toluene (KF<100 μg/mL) under ice-MeOH cooling. To this solution was added boron trichloride gas (1.42 kg), keeping the temperature under 7° C.

To a 22 L three neck round bottom flask, equipped with a nitrogen inlet and an overhead stirrer, was added dry toluene (10.2 L, KF<100 μg/mL). To this solution was added 2.214 kg of 4-chloroaniline and warmed up to 55° C. to give a homogeneous solution. The solution was cooled to 10°–20° C.

The solution of 4-chloroaniline was transferred into the 10 L dropping funnel and added to the solution of boron trichloride, keeping the temperature at least below 10° C. with a dry ice-acetone bath. The reaction mixture turned into a heavy suspension.

The suspension was stirred at room temperature for 30 minutes. To this suspension was added 4-chlorobutyronitrile (991 mL, 11 mole), in one portion, under a nitrogen atmosphere.

After 30 minutes of stirring, gallium trichloride (2.324 kg) was added to the mixture under nitrogen atmosphere. The resulting exothermic reaction raised the temperature of the mixture to about 40° C. This solution was stirred at 100° C. for 5 hours, giving a biphasic reaction mixture (70–75% yield). The solution was cooled to 40° C. The solution was diluted with toluene (3 L) and DI water (11 L). The organic phase was separated. The pH of the aqueous layer was 0.2. The organic layer was washed with DI water (11 L) to remove 4-chloroaniline. The final organic layer (25 L) contained 70 mg/mL of the product (1800 g; 72% yield). The solution was concentrated under reduced pressure to give 16 L of a 113 mg/mL (0.5 M) solution of the product (KF<170 μg/mL). This solution was used directly in the next step.

Employing the procedures substantially as described above for preparation of ketone 3 but substituting $INCl_3$ or $FeCl_3$ for the $AlCl_3$ and $GaCl_3$, similar results are obtained.

Preparation of 4

A solution of the crude product from the previous reaction in THF (820 ml) was treated with t-BuOK (151 ml, 0.257 mol) in THF via addition funnel at a moderate rate (small exotherm was observed). The reaction was complete within 30 minutes and was quenched with $H_2O$ followed by the addition of NaCl to saturate the aqueous layer. The organic layer was washed with 1N HCl, dried over $MgSO_4$, filtered, and concentrated in vacuo to obtain 33.5 g (41–44% overall yield when the $AlCl_3$ procedure was used) of the desired product, 4.

Note: Excess t-BuOK must be added to compensate for the remaining 4-chlorobutyronitrile from the previous reaction when $AlCl_3$ was used. The latter was converted, under the reaction conditions, to cyclopropyl nitrile which was easily removed in vacuo. Using the $GaCl_3$ procedure there was no 4-chlorobutyronitrile present.

Preparation of 5

Potassium cyanate (40 g, 0.484 mol) was dissolved in $H_2O$ (80 ml) and this solution was added to a cold solution (+9° C.) of the cyclopropyl ketone, 4, (39.9 g, 0.20 mol) in acetic acid (800 ml). After the addition was completed, the cooling bath was removed. The reaction was monitored carefully for disappearance of starting material, (4), since prolonged aging resulted in higher level of impurities. The reaction was complete within 1–1.5 hours at which time, $H_2O$ (3300 ml) was added and the resulting slurry was allowed to stir for 2 hours. The solid was isolated by filtration and the cake was washed with $H_2O$ (1400 ml) and dried in vacuo (40° C.) to give the desired product, 5, 38.4 g (87% yield). This yield included the 2 impurities at 3.3 min and 6.7 min (HPLC retention times).

The cyclopropyl quinazolinone, 5, (38.3 g) was suspended in hexanes (960 ml) and heated at reflux for 10–15 minutes. After cooling and filtration, 35.7 g were obtained (81% overall yield with 93% recovery). By LC assay, the 6.7–6.9 min impurity peak (the Nacetyl derivative 11) had decreased from 10% A to 1.2% A; them was no effect on the 3.3 min peak.

Preparation of 7

NaI (10.2 g, 68.03 mmol) was dried by heating to +80° C. under high vacuum for 4 hours.

The quinazolinone, 5, (10 g, 45.35 mmol) was azeotropically dried with toluene and then dissolved in DMF (80 ml) in a 3-neck, round bottom flask equipped with a mechanical stirrer and an addition funnel. Additional DMF (20 ml) was used for rinses. The reaction vessel was cooled to 0° C. and LHMDS (55 ml, 55.0 mmol in THF, 1 M) was added via an addition funnel maintaining the temperature below +5° C. After 15–30 minutes, 4-methoxybenzyl chloride, fi, (8 ml, 59.0 mmol) was added followed by NaI (10.2 g, 68.03 mmol). The cooling bath was then removed and the reaction was allowed to warm to RT. The reaction was heated to 60° C. and allowed to age overnight. With approximately 2% A of starting material (5) present, the reaction mixture was cooled to RT, concentrated in vacuo, and the concentrate was flushed with acetonitrile (2×50 ml). Acetonitrile (140 ml) was then added to the concentrate, with stirring, followed by slow addition of water (70 ml). The resulting slurry was allowed to stir for 10 minutes and the product was filtered. The cake was washed with acetonitrile-water (75 ml, 2:1) and dried in vacuo (40° C.) giving 7, 11.3 g (73%).

Preparation of 9

To a 3-neck, round bottom flask, THF (32 ml) was added followed by 2-ethynyl pyridine, 8, (800 gl, 7.92 mmol). The solution was cooled to −78° C. and n-BuLi (4.8 ml, 7.63 mmol in hexane, 1 M) was added dropwise maintaining the temperature below −70° C. After the addition was complete, the solution became heterogeneous and was aged for 2 hours at −78° C. The benzylated quinazolinone, 7, (2 g, 5.87 mmol) was added under a $N_2$ blanket. The reaction mixture was warmed to −15° C. and was aged for 12 hours until less than 1 A%, by LC, of starting material, 7, was present. The reaction mixture was quenched with 1 M citric acid followed by extractive workup using EtOAc and saturation of aqueous layer with NaCl. The organic layer was washed with saturated $NaHCO_3$ solution, dried over $MgSO_4$, filtered and concentrated in vacuo. Hexanes (20 ml) and ethyl acetate (5 ml) were added to the concentrate and the resulting slurry was stirred overnight. After filtration, the cake was washed with hexanesethylacetate (25 ml, 4:1) and dried in a vacuum oven to give 2.2 g (86%) of the desired product, 9. The LC purity, using 65:35% to 100.0% acetonitrile:water (in 35 minutes), was 96 A% (uncorrected).

Preparation of 10

A quantity of 70 mg (0.16 mmole) of 9 was treated with a solution of 3.2 ml of trifluoroacetic acid in 4.5 ml of methylene chloride for 96 hours under argon. The solvents were evaporated and the residue was partitioned between $CHCl_3$ and 10% w/v aqueous $Na_2CO_3$. The organic layer was dried over $Na_2SO_4$, filtered and evaporated to 38 mg of an amorphous solid (73%).

NMR ($CDCl_3$): 0.58–0.72 (m, 1H), 0.73–0.90 (m, 2H), 0.91–1.04 (m, 1H), 1.47–1.60 (m, 1H), 5.85 (s, 1H), 6.78 (d, J=8Hz, 1H), 7.15 (dd, J−8, 2Hz, 1H), 7.20–7.28 (m, 1H), 7.39 (d, J=8Hz, 1H), 7.52 (d, J−2Hz, 1H), 7.63 (td, J=8,2Hz, 1H), 8.58 (d, J=4Hz, 1H), 9.13 (s, 1H).

What is claimed is:

1. A process for the preparation of a compound of structural formula

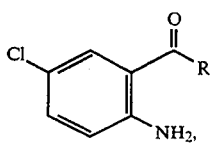

wherein R is

or (CH$_2$)$_3$Cl; which comprises treating a mixture of boron trichloride and a compound of structural formula 1

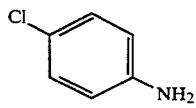

in an organic solvent with a compound of formula RCN (2) and the auxiliary Lewis acid gallium trichloride at 15°–35° C., followed by heating at about 100°–130° C. for about 3–6 hours, to produce a compound of structural formula:

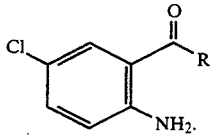

2. The process of claim 1 wherein the organic solvent for compound 1 is methylene chloride, toluene, xylene, chlorobenzene, or tetrachloroethane.

3. The process of claim 1, wherein R is -(CH$_2$)$_3$Cl.

4. The process of claim 2, wherein R is -(CH$_2$)$_3$Cl.

5. A process for the preparation of a compound of the structural formula:

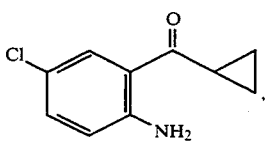

which comprises the steps of (a) mixing one equivalent of 4-chloroaniline in toluene with about one equivalent of BCl$_3$ at a temperature range of about −10° to about 10° C., to give a mixture;

(b) warming the mixture to between about 15° and about 35° C.;

(c) adding thereto about 0.5 equivalents of 4-chlorobutyronitrile;

(d) adding about 0.55 equivalents of GaCl$_3$;

(e) stirring for about 4 hours at about 100° C., to give compound 4.

* * * * *